(12) United States Patent
Abe et al.

(10) Patent No.: US 9,109,971 B2
(45) Date of Patent: Aug. 18, 2015

(54) RESPIRATORY CONDITION ANALYSIS APPARATUS, RESPIRATORY CONDITION DISPLAY APPARATUS, PROCESSING METHOD THEREIN, AND PROGRAM

(75) Inventors: Mototsugu Abe, Kanagawa (JP); Chika Myoga, Tokyo (JP); Masayuki Nishiguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 918 days.

(21) Appl. No.: 13/308,650

(22) Filed: Dec. 1, 2011

(65) Prior Publication Data
US 2012/0150054 A1    Jun. 14, 2012

(30) Foreign Application Priority Data
Dec. 8, 2010 (JP) ................................. 2010-273635

(51) Int. Cl.
*A61B 7/00* (2006.01)
*G01L 25/00* (2006.01)
*G01L 21/06* (2006.01)
*A61B 7/02* (2006.01)
*A61B 5/08* (2006.01)

(52) U.S. Cl.
CPC .............. *G01L 25/00* (2013.01); *A61B 7/003* (2013.01); *G01L 21/06* (2013.01); *A61B 5/0816* (2013.01); *A61B 7/02* (2013.01)

(58) Field of Classification Search
CPC ........ A61B 7/003; A61B 7/02; A61B 5/0816; G10L 25/00

USPC ............................................. 600/529–543, 586
See application file for complete search history.

(56) References Cited

U.S. PATENT DOCUMENTS

| 5,165,417 A | * | 11/1992 | Murphy, Jr. ................... 600/529 |
| 6,261,238 B1 | * | 7/2001 | Gavriely ....................... 600/532 |
| 2009/0171231 A1 | * | 7/2009 | Caro et al. .................... 600/529 |
| 2011/0125044 A1 | * | 5/2011 | Rhee et al. .................... 600/534 |
| 2011/0230777 A1 | * | 9/2011 | Fu ................................ 600/529 |
| 2012/0157857 A1 |   | 6/2012 | Abe et al. |

FOREIGN PATENT DOCUMENTS

JP    2005-066045 A    3/2005

* cited by examiner

*Primary Examiner* — Navin Natnithithadha
*Assistant Examiner* — Eric Messersmith
(74) *Attorney, Agent, or Firm* — Hazuki International, LLC

(57) ABSTRACT

A respiratory condition analysis apparatus includes a respiratory signal acquisition section configured to acquire a time-series respiratory signal including respiratory sound of a living body, a respiratory segment identification section configured to identify a respiratory segment that is a time segment including the respiratory sound in the respiratory signal, a feature value generation section configured to generate a predetermined feature value of the respiratory signal for the identified respiratory segment, and a respiratory abnormality degree generation section configured to generate a degree of abnormality of the respiratory sound included in the respiratory signal on the basis of the feature value.

14 Claims, 9 Drawing Sheets

RESPIRATORY CONDITION ANALYSIS APPARATUS, RESPIRATORY CONDITION DISPLAY APPARATUS, PROCESSING METHOD THEREIN, AND PROGRAM

BACKGROUND

The present disclosure relates to respiratory condition analysis apparatuses, and, more particularly, to a respiratory condition analysis apparatus and a respiratory condition display apparatus which analyze the respiratory condition of a living body such as a human being on the basis of a time-series respiratory signal including respiratory sound of the human being, a processing method therein, and a program for causing a computer to execute the method.

Monitoring of respiratory sound using a stethoscope or the like has been widely performed to check a biological condition. A respiratory condition analysis apparatus for analyzing a respiratory condition on the basis of a time-series respiratory signal including respiratory sound monitored by a stethoscope or the like has been developed.

For example, an apparatus for calculating spectrum information by performing Fast Fourier Transform (FFT) processing on respiratory sound data in each of a plurality of time segments having different lengths set in advance, and detecting abnormal sound by analyzing the spectrum information has been proposed (see, for example, Japanese Unexamined Patent Application Publication No. 2005-066045). In this related art, abnormal sound is detected by determining whether a dominant frequency component (formant) defining the type of abnormal sound has lasted for a predetermined period on the basis of a spectral envelope on a sound spectrogram and the sound spectrogram. For example, when a high-frequency component (500 Hz to 1000 Hz) lasts for a period equal to or shorter than 25 milliseconds at an intensity equal to or greater than a predetermined intensity, it is determined that the high-frequency component is generated by a discontinuous rale. When a frequency equal to or higher than 400 Hz lasts for a period equal to or longer than 250 milliseconds at an intensity equal to or greater than a predetermined intensity, it is determined that the frequency is generated by a continuous rale. Each of the discontinuous rale and the continuous rale is adventitious sound included in respiratory sound, and is determined to be abnormal sound.

SUMMARY

In the above-described related art, time segments are set in advance before abnormal sound included in respiratory sound is detected and determination is performed by measuring a period during which a signal having a specific frequency component has lasted. This method incorporates a method used in speech recognition based on a speech generation model. The appropriateness of applying the same model as that used for speech recognition to the determination of abnormality of respiratory sound is not proved. Accordingly, various normal conditions and various abnormal conditions of many people may not be accurately detected.

It is desirable to accurately detect various normal conditions or various abnormal conditions by quantifying the normality or abnormality of respiration of a living body.

According to an embodiment of the present disclosure, there is provided a respiratory condition analysis apparatus, a processing method of the respiratory condition analysis apparatus, and a program. The respiratory condition analysis apparatus includes a respiratory signal acquisition section configured to acquire a time-series respiratory signal including respiratory sound of a living body, a respiratory segment identification section configured to identify a respiratory segment that is a time segment including the respiratory sound in the respiratory signal, a feature value generation section configured to generate a predetermined feature value of the respiratory signal for the identified respiratory segment, and a respiratory abnormality degree generation section configured to generate a degree of abnormality of the respiratory sound included in the respiratory signal on the basis of the feature value. As a result, the degree of abnormality of respiratory sound in a time segment in a respiratory signal is quantified.

The respiratory condition analysis apparatus may further include a respiratory sound correlation degree generation section configured to generate a degree of correlation between a respiratory sound model set in advance and the respiratory signal and a respiratory sound reliability degree generation section configured to generate a degree of reliability of respiratory sound representing respiratory sound likeness of the respiratory signal on the basis of the correlation degree. The respiratory segment identification section may identify the respiratory segment on the basis of the respiratory sound reliability degree. As a result, a respiratory segment is identified on the basis of the degree of correlation between a respiratory signal and a respiratory sound model.

In the respiratory condition analysis apparatus, the respiratory sound correlation degree generation section may include a time frequency conversion unit configured to perform time frequency conversion on the respiratory signal and generate a time frequency signal, a basis conversion unit configured to project the time frequency signal into a basis vector of the respiratory sound model and generate a basis conversion signal, and a nonlinear transformation unit configured to perform predetermined nonlinear transformation on the basis conversion signal and output the correlation degree. As a result, the correlation degree is generated on the basis of the base vector of the respiratory sound model, and a respiratory segment is identified on the basis of the correlation degree.

The respiratory condition analysis apparatus may further include a respiratory abnormality determination section configured to determine whether the respiratory sound is in a normal respiratory condition or an abnormal respiratory condition on the basis of the abnormality degree. As a result, respiratory abnormality is determined on the basis of a quantified abnormality degree. In this case, the respiratory abnormality determination section may further determine an intermediate condition between the normal respiratory condition and the abnormal respiratory condition.

The respiratory condition analysis apparatus may further include a respiratory rate measurement unit configured to measure the number of the identified respiratory segments per unit time and output a result of the measurement as the number of respirations. As a result, the number of respirations is output as one of respiratory conditions.

According to another embodiment of the present disclosure, there is provided a respiratory condition display apparatus including a respiratory signal acquisition section configured to acquire a time-series respiratory signal including respiratory sound of a living body, a respiratory segment identification section configured to identify a respiratory segment that is a time segment including the respiratory sound in the respiratory signal, a feature value generation section configured to generate a predetermined feature value of the respiratory signal for the identified respiratory segment, a respiratory abnormality degree generation section configured to generate a degree of abnormality of the respiratory sound included in the respiratory signal on the basis of the feature value, a respiratory abnormality determination section configured to determine whether the respiratory sound is in a normal respiratory condition or an abnormal respiratory condition on the basis of the abnormality degree, and a display section configured to display a result of the determination of the respiratory sound. As a result, the respiratory abnormality of respiratory sound in a time segment in a respiratory signal is displayed.

According to an embodiment of the present disclosure, it is possible to accurately detect various normal conditions or various abnormal conditions by quantifying the normality or abnormality of respiration of a living body.

DETAILED DESCRIPTION OF EMBODIMENTS

Embodiments of the present disclosure (hereinafter referred to as "embodiments") will be described below. The descriptions will be made in the following order.
1. First Embodiment (Example Using Feature Value of Respiratory Signal)
2. Second Embodiment (Example Using Feature Value and Correlation Degree of Respiratory Signal)

1. First Embodiment

Configuration of Respiratory Condition Display System

Figure 1:
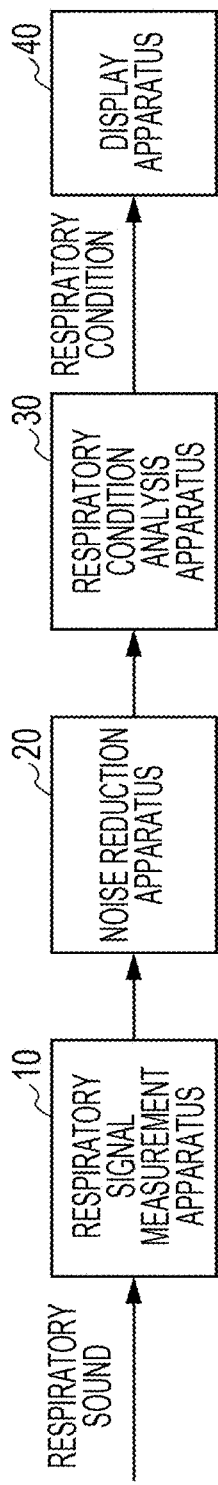
FIG. 1 is a diagram illustrating an exemplary configuration of a respiratory condition display system according to an embodiment of the present disclosure.

FIG. 1 is a diagram illustrating an exemplary configuration of a respiratory condition display system according to an embodiment of the present disclosure. This respiratory condition display system includes a respiratory signal measurement apparatus 10, a noise reduction apparatus 20, a respiratory condition analysis apparatus 30, and a display apparatus 40.

The respiratory signal measurement apparatus 10 measures a time-series respiratory signal including respiratory sound of a living body such as a human being. A stethoscope can be used as the respiratory signal measurement apparatus 10. A microphone placed near a throat or a pressure sensor or an acceleration sensor that is in contact with skin on a throat or chest may perform measurement.

The noise reduction apparatus 20 performs noise reduction processing on a respiratory signal measured by the respiratory signal measurement apparatus 10. Ambient sound around a living body and heartbeat sound of the living body are assumed to be noise. The noise reduction apparatus 20 is, for example, a band-pass filter or a low cut filter that passes a frequency component of respiratory sound.

The respiratory condition analysis apparatus 30 analyzes a respiratory condition on the basis of the respiratory sound included in the respiratory signal that has passed through the noise reduction apparatus 20. The respiratory condition is, for example, respiratory abnormality representing whether respiration is normally or abnormally performed or the number of respirations per unit time.

The display apparatus 40 is a monitor for displaying the respiratory condition analyzed by the respiratory condition analysis apparatus 30. The display apparatus 40 is, for example, a Liquid Crystal Display (LCD). The display apparatus 40 is an example of a display section in claims.

[Schematic Configuration of Respiratory Condition Analysis Apparatus]

Figure 2:
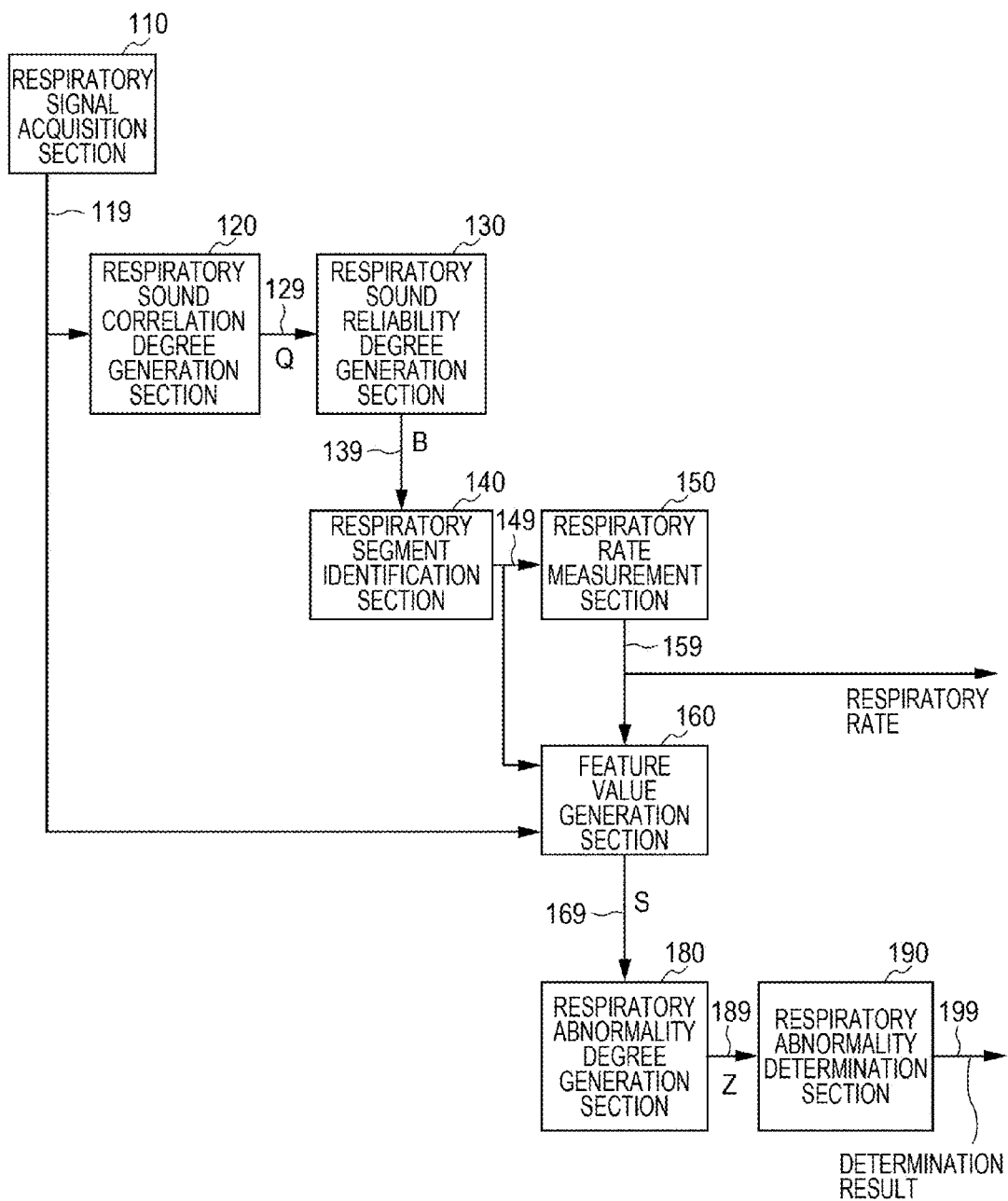
FIG. 2 is a diagram illustrating an exemplary configuration of a respiratory condition analysis apparatus according to a first embodiment of the present disclosure.

FIG. 2 is a diagram illustrating an exemplary configuration of the respiratory condition analysis apparatus 30 according to the first embodiment of the present disclosure. The respiratory condition analysis apparatus 30 includes a respiratory signal acquisition section 110, a respiratory sound correlation degree generation section 120, a respiratory sound reliability degree generation section 130, a respiratory segment identification section 140, a respiratory rate measurement section 150, a feature value generation section 160, a respiratory abnormality degree generation section 180, and a respiratory abnormality determination section 190.

The respiratory signal acquisition section 110 acquires a time-series respiratory signal including respiratory sound of a living body such as a human being. In this example, the respiratory signal that has passed through the respiratory signal measurement apparatus 10 and the noise reduction apparatus 20 is input into the respiratory signal acquisition section 110 and the respiratory signal acquisition section 110 acquires the respiratory signal. The respiratory signal acquired by the respiratory signal acquisition section 110 is supplied to the respiratory sound correlation degree generation section 120 and the feature value generation section 160 via a signal line 119.

The respiratory sound correlation degree generation section 120 generates the degree of correlation between the respiratory signal supplied from the respiratory signal acquisition section 110 and a respiratory sound model set in advance. The respiratory sound model is created on the basis of many respiratory sound learning samples, and has to largely reflect the characteristic of respiratory sound. The respiratory sound correlation degree generated by the respiratory sound correlation degree generation section 120 is supplied to the respiratory sound reliability degree generation section 130 via a signal line 129.

The respiratory sound reliability degree generation section 130 generates the degree of reliability of respiratory sound representing respiratory sound likeness of a respiratory signal every discrete time on the basis of the respiratory sound correlation degree generated by the respiratory sound correlation degree generation section 120. The respiratory sound reliability degree generated by the respiratory sound reliability degree generation section 130 is supplied to the respiratory segment identification section 140 via a signal line 139.

The respiratory segment identification section 140 identifies a respiratory segment that is a time segment including respiratory sound in the respiratory signal on the basis of the respiratory sound reliability degree supplied from the respiratory sound reliability degree generation section 130. The respiratory segment identified by the respiratory segment identification section 140 is supplied to the respiratory rate measurement section 150 and the feature value generation section 160.

The respiratory rate measurement section 150 measures the number of respirations per unit time by counting the number of respiratory segments identified by the respiratory segment identification section 140. The unit time is, for example, one minute. The number of respirations measured by the respiratory rate measurement section 150 is a display target to be output to the display apparatus 40 via a signal line 159 and be displayed as one of respiratory conditions. The number of respirations may be used to generate a feature value. In this case, the number of respirations is supplied to the feature value generation section 160 via the signal line 159.

The feature value generation section 160 generates a feature value for the respiratory segment identified by the respiratory segment identification section 140 in the respiratory signal supplied from the respiratory signal acquisition section 110. As the feature value of the respiratory signal, a signal amplitude value, the change in the amplitude value, a spectrum value, the change in the spectrum value, a zero-crossing rate, or the change in the zero-crossing rate obtained directly from the respiratory segment in the respiratory signal can be used. For the sake of simplification, such values obtained in a target respiratory segment are integrated by averaging, weighted averaging, or square mean. The number of respirations measured by the respiratory rate measurement section 150 near the respiratory segment may be used as the feature value. Basis conversion and nonlinear transformation may be performed on the feature value as appropriate. The feature value generated by the feature value generation section 160 is supplied to the respiratory abnormality degree generation section 180 via a signal line 169.

The respiratory abnormality degree generation section 180 generates a degree of abnormality of the respiratory sound included in the respiratory signal supplied from the respiratory signal acquisition section 110 on the basis of the feature value generated by the feature value generation section 160. The respiratory abnormality degree generated by the respiratory abnormality degree generation section 180 is supplied to the respiratory abnormality determination section 190 via a signal line 189.

The respiratory abnormality determination section 190 determines whether the respiratory sound included in the respiratory signal supplied from the respiratory signal acquisition section 110 is in a normal respiratory condition or an abnormal respiratory condition on the basis of the respiratory abnormality degree generated by the respiratory abnormality degree generation section 180. A result of the determination performed by the respiratory abnormality determination section 190 is a display target to be output to the display apparatus 40 via a signal line 199 and be displayed as one of respiratory conditions.

[Generation of Respiratory Sound Correlation Degree]

Figure 3:
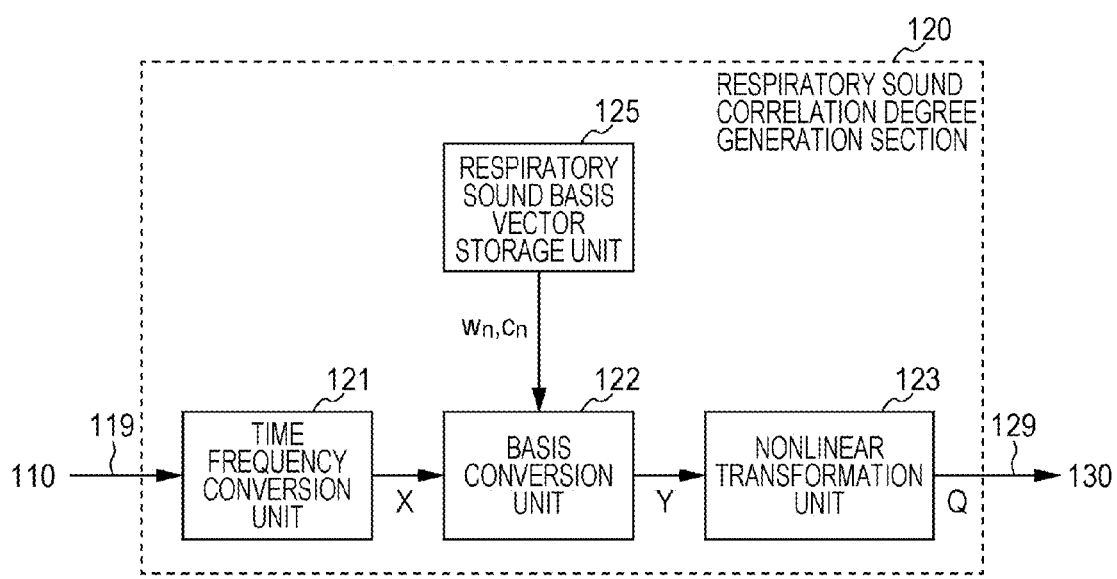
FIG. 3 is a diagram illustrating an exemplary configuration of a respiratory sound correlation degree generation section according to an embodiment of the present disclosure.

FIG. 3 is a diagram illustrating an exemplary configuration of the respiratory sound correlation degree generation section 120 according to an embodiment of the present disclosure. The respiratory sound correlation degree generation section 120 includes a time frequency conversion unit 121, a basis conversion unit 122, a nonlinear transformation unit 123, and a respiratory sound basis vector storage unit 125.

The time frequency conversion unit 121 performs time frequency conversion on the respiratory signal supplied from the respiratory signal acquisition section 110 and generates a time frequency signal $X(t, k)$. As the time frequency conversion, short-time Fourier transform may be performed. Alternatively, the group of band-pass filters or wavelet transform that can provide a similar effect may be used or performed. In addition, frequency axis distortion such as Mel frequency conversion may be performed on a spectrum acquired by the short-time Fourier transform.

Figure 4:
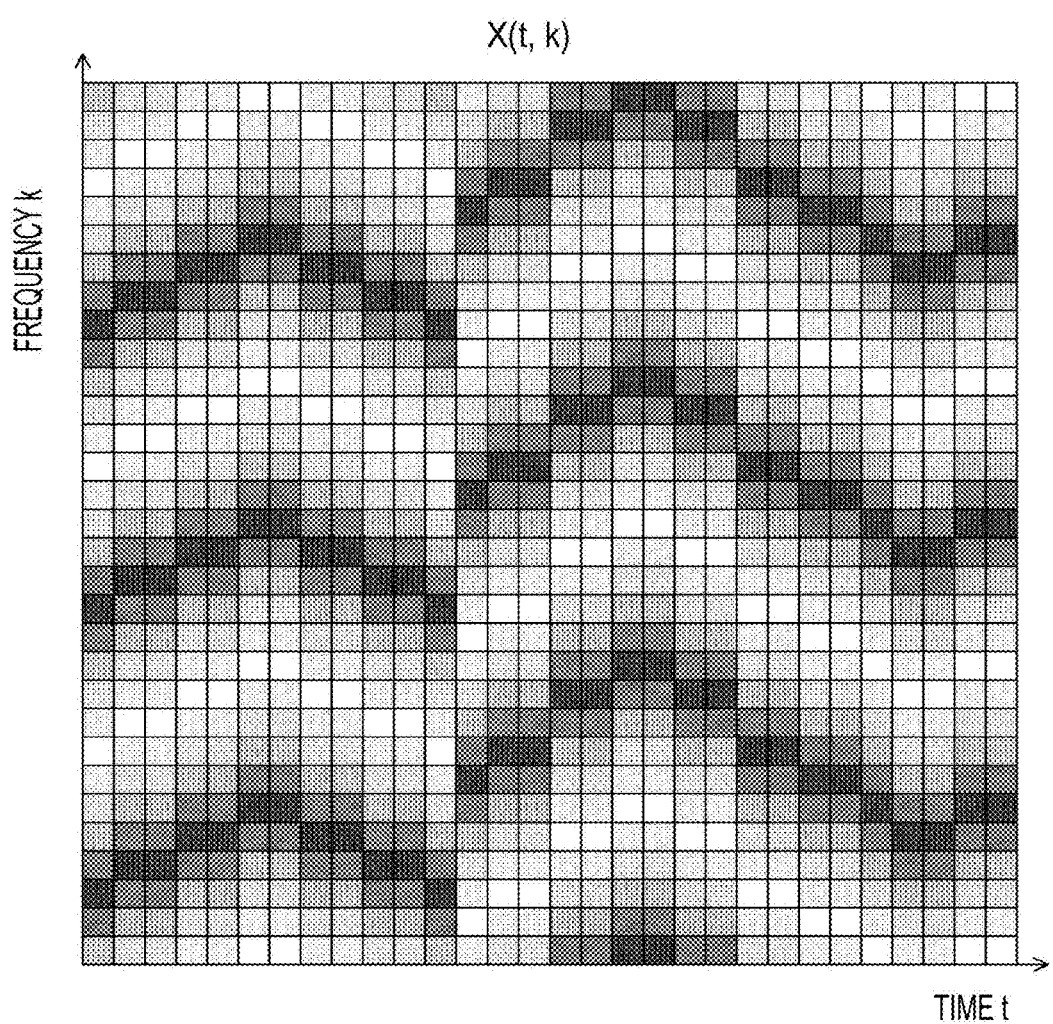
FIG. 4 is a diagram illustrating an example of a time frequency signal according to an embodiment of the present disclosure.

The time frequency signal obtained by the time frequency conversion by the time frequency conversion unit 121 is as illustrated in, for example, FIG. 4. A time t represents a discrete time, and a frequency k represents a discrete frequency. A point of intersection of the time t and the frequency k represents the time frequency signal $X(t, k)$. The depth of shading represents the strength of a time frequency signal. The time frequency signal is strong at a dark portion and weak at a light portion. That is, at a certain time t, the time frequency signal indicates a certain undulation in accordance with the frequency k. The undulation changes with time.

The respiratory sound basis vector storage unit 125 stores a basis vector $w_n(k)$ and a constant $c_n$ of a respiratory sound model set in advance. The basis vector $w_n(k)$ is a function for the frequency k, and is present for each basis number n. The constant $c_n$ is a constant associated with each basis, and is used to adjust the position of an origin. As will be described later, the basis vector and the constant of the respiratory sound model can be generated by, for example, giving a correct answer for respiratory sound or nonrespiratory sound to a plurality of respiratory sound learning samples.

The basis conversion unit 122 projects the time frequency signal $X(t, k)$ into the basis vector $w_n(k)$ of the respiratory sound model and generates a basis conversion signal $Y(t, n)$. The basis conversion signal $Y(t, n)$ is acquired by the following equation.

$$Y(t, n) = \sum_k X(t, k) w_n(k) + c_n$$

The basis conversion signal $Y(t, n)$ acquired by the basis conversion unit 122 represents the degree of similarity between the frequency spectra of the respiratory sound and the respiratory sound model. Since a basis vector is present for each basis number n, a case in which there is similarity to one of bases and no similarity to the other ones of the bases may occur. In this case, the respiratory sound reliability degree generation section 130 determines combinations of evaluation target bases when quantifying a respiratory sound reliability degree.

The nonlinear transformation unit 123 performs nonlinear transformation on the basis conversion signal $Y(t, n)$ and outputs a respiratory sound correlation degree $Q(t, n)$. The nonlinear transformation is, for example, a sigmoid function, a logarithmic function, an exponential function, a square root, or a Gaussian function. In preparation for a case in which the range of the basis conversion signal Y(t, n) is too expanded, the nonlinear transformation is performed to reduce the range. When it is assumed that a function used for nonlinear transformation is F, the respiratory sound correlation degree Q(t, n) is obtained by the following equation.

$$Q(t,n)=F(Y(t,n))$$

Instead of nonlinear transformation, non-transformation or linear transformation may be performed.

Figure 5:
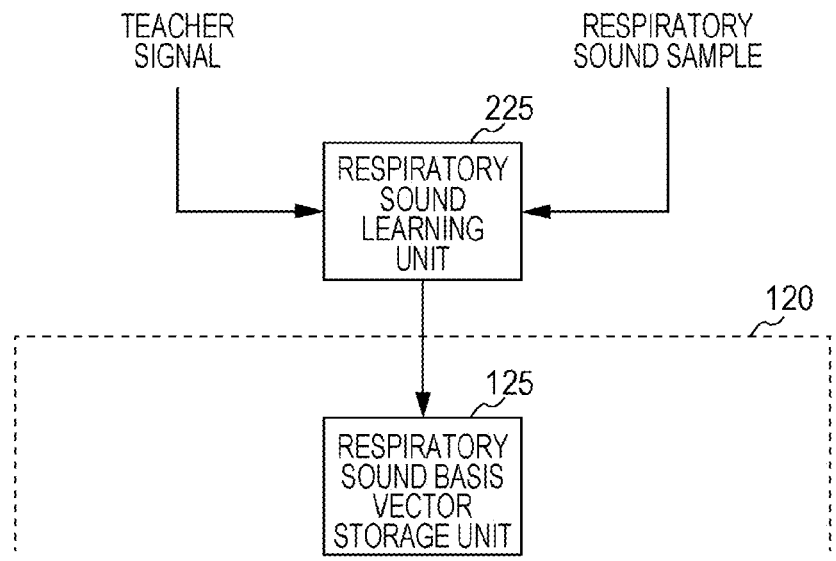
FIG. 5 is a diagram illustrating an exemplary learning process of a respiratory sound basis vector according to an embodiment of the present disclosure.

FIG. 5 is a diagram illustrating an exemplary learning process of a respiratory sound basis vector according to an embodiment of the present disclosure. It is desired that many respiratory sound learning samples be prepared. A respiratory sound learning unit 225 gives a correct answer, for example, a teacher signal indicating that sound is respiratory sound or nonrespiratory sound, to each respiratory sound sample. For example, by using an optimization method such as the steepest descent method or the Newton method, a respiratory sound sample is learned and the n-dimensional basis vector $w_n(k)$ that is a function for the frequency k and the constant $c_n$ are generated. The generated basis vector $w_n(k)$ and the generated constant $c_n$ are stored in the respiratory sound basis vector storage unit 125.

[Generation of Respiratory Sound Reliability Degree]

Figure 6:
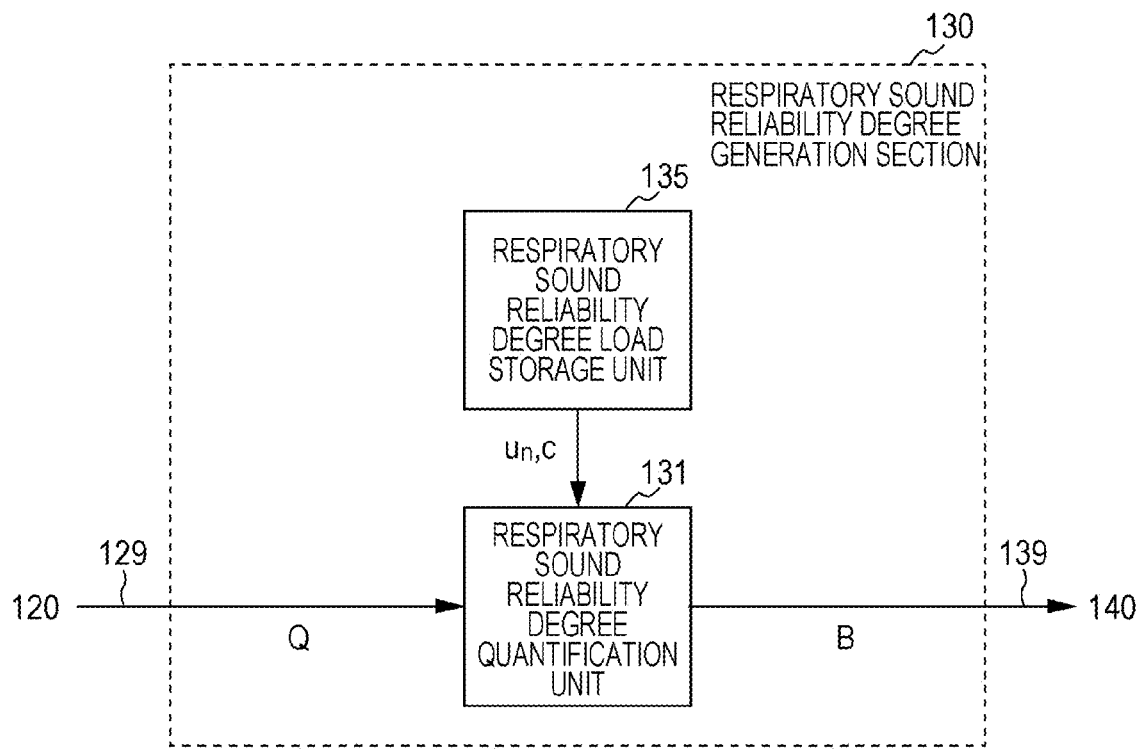
FIG. 6 is a diagram illustrating an exemplary configuration of a respiratory sound reliability degree generation section according to an embodiment of the present disclosure.

FIG. 6 is a diagram illustrating an exemplary configuration of the respiratory sound reliability degree generation section 130 according to an embodiment of the present disclosure. The respiratory sound reliability degree generation section 130 includes a respiratory sound reliability degree quantification unit 131 and a respiratory sound reliability degree load storage unit 135.

The respiratory sound reliability degree load storage unit 135 stores loads $u_n$ and $v_n$ and a constant c which are necessary for quantification of a respiratory sound reliability degree. The loads $u_n$ and $v_n$ are present for each basis number n. The constant c is used to adjust the position of an origin, and is common to each basis.

The respiratory sound reliability degree quantification unit 131 quantifies a respiratory sound reliability degree B(t) representing respiratory sound likeness of a respiratory signal every discrete time on the basis of the respiratory sound correlation degree Q(t, n) generated by the respiratory sound correlation degree generation section 120. The respiratory sound reliability degree B(t) is obtained by the following equation, the linear weighted sum of the respiratory sound correlation degrees Q(t, n).

$$B(t) = \sum_n u_n Q(t, n) + c$$

It is possible to remove an exceptional value by adding a time smoothing addition term including a multiplication in the center of a time t with a window function and spectral averaging over a time segment. As a result, an instantaneous change in a respiratory sound conversion pattern is reduced, and a score becomes temporally stable. In this case, the respiratory sound reliability degree B(t) is obtained by the following equation.

$$B(t) = \sum_n u_n Q(t, n) + v_n \overline{Q}(t, n) + c$$

It is possible to take a temporal change in respiratory sound into consideration and improve correspondence to various respiratory sound patterns by adding a time smoothing difference term indicating the difference between results of time smoothing additions performed at slightly different times. In this case, the respiratory sound reliability degree B(t) is obtained by the following equation.

$$B(t) = \sum_n u_n Q(t, n) + v_n \tilde{Q}(t, n) + c$$

Figure 7:
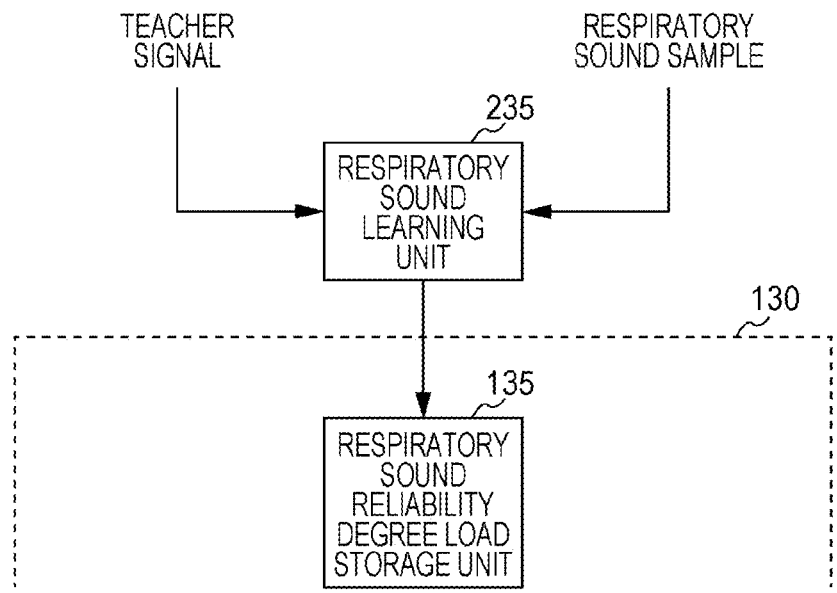
FIG. 7 is a diagram illustrating an exemplary learning process of a respiratory sound reliability degree load according to an embodiment of the present disclosure.

FIG. 7 is a diagram illustrating an exemplary learning process of a respiratory sound reliability degree load according to an embodiment of the present disclosure. Like the respiratory sound learning unit 225, a respiratory sound learning unit 235 gives a correct answer, for example, a teacher signal indicating that sound is respiratory sound or nonrespiratory sound, to each respiratory sound sample. By using an optimization method such as the steepest descent method or the Newton method, loads and a constant with which the best discrimination between respiratory sound and nonrespiratory sound is made can be generated. The generated loads $u_n$ and $v_n$ and the constant c are stored in the respiratory sound reliability degree load storage unit 135.

[Identification of Respiratory Segment]

Referring back to FIG. 2, the respiratory segment identification section 140 will be described. The respiratory segment identification section 140 identifies a respiratory segment on the basis of the respiratory sound reliability degree B(t) supplied from the respiratory sound reliability degree generation section 130. For example, as described below, it can be determined that a respiratory condition is set when the respiratory sound reliability degree B(t) is equal to or larger than a predetermined threshold value TH1 and a nonrespiratory condition is set when the respiratory sound reliability degree B(t) is not equal to or larger than the threshold value TH1.

$B(t) \geq TH1 \rightarrow$ respiratory condition $B(t) < TH1 \rightarrow$ nonrespiratory condition Thus, in each discrete time t, it is determined whether the respiratory condition or the nonrespiratory condition is set. By following the transition between the respiratory condition and the nonrespiratory condition, each respiratory segment can be identified. The respiratory rate measurement section 150 can measure the number of respirations per unit time by counting the number of respiratory segments identified by the respiratory segment identification section 140.

[Generation of Degree of Respiratory Abnormality]

Figure 8:
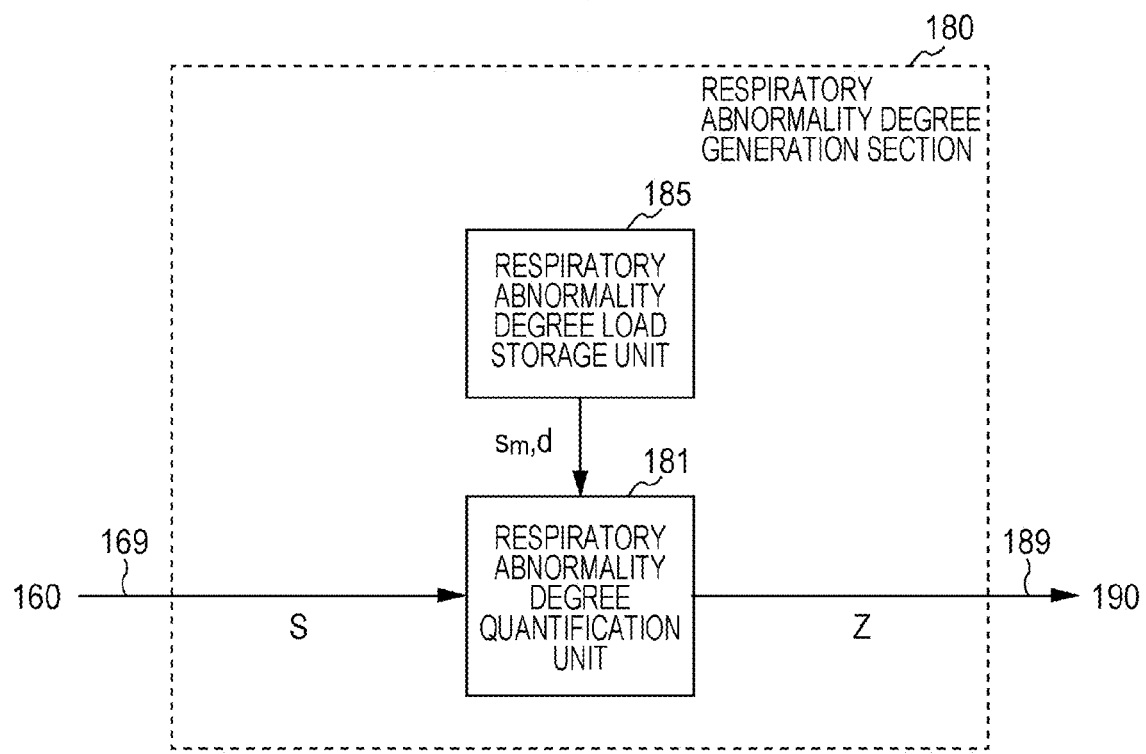
FIG. 8 is a diagram illustrating an exemplary configuration of a respiratory abnormality degree generation section according to an embodiment of the present disclosure.

FIG. 8 is a diagram illustrating an exemplary configuration of the respiratory abnormality degree generation section 180 according to an embodiment of the present disclosure. The respiratory abnormality degree generation section 180 includes a respiratory abnormality degree quantification unit 181 and a respiratory abnormality degree load storage unit 185.

The respiratory abnormality degree load storage unit 185 stores a load $s_m$ and a constant d which are necessary for quantification of the degree of respiratory abnormality. Here, m represents the number of a feature value, and the load $s_m$ is present for each feature value. The constant d is used to adjust the position of an origin, and is common to each basis.

The respiratory abnormality degree quantification unit 181 quantifies the degree of abnormality of respiratory sound on the basis of a feature value S(l, m) generated by the feature value generation section 160. Here, l represents the number of each respiratory segment. That is, it is assumed that, in the feature value generation section 160, m kinds of feature values are generated for the respiratory segment l and vectorized. For the quantification of the degree of respiratory abnormality, a so-called statistical identification method such as a Bayes decision apparatus, a linear discrimination apparatus, a generalized linear discrimination apparatus, a neural network, a support vector machine (SVM), a Boosting method, or a Gaussian mixture method can be used. For example, in the case of a linear discrimination apparatus, a respiratory abnormality degree Z(l) can be quantified by the linear weighted sum of feature values as represented by the following equation.

$$Z(l) = \sum_m s_m S(l, m) + d$$

Figure 9:
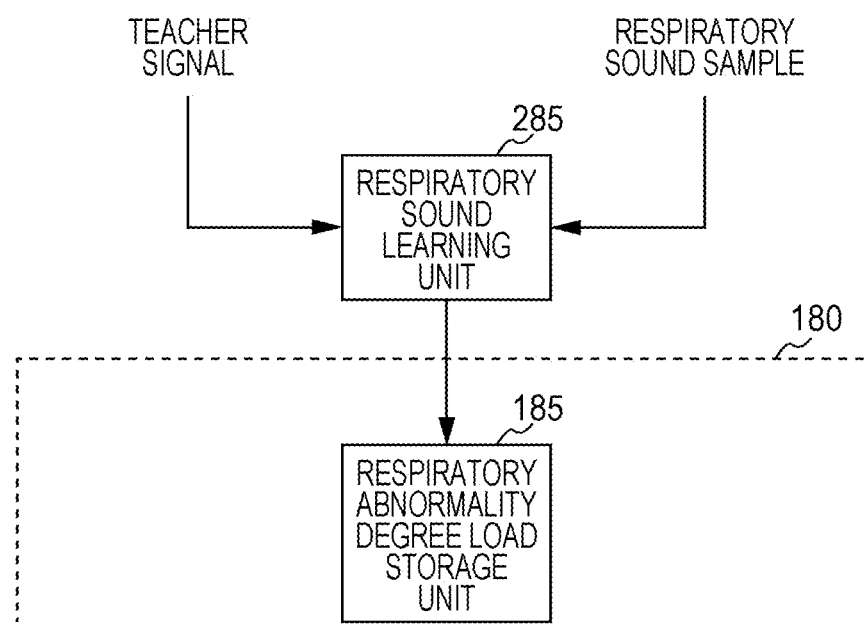
FIG. 9 is a diagram illustrating an exemplary learning process of a respiratory abnormality load according to an embodiment of the present disclosure.

FIG. 9 is a diagram illustrating an exemplary learning process of a respiratory abnormality degree load according to an embodiment of the present disclosure. A respiratory sound learning unit 285 gives a correct answer, for example, a teacher signal indicating that sound is normal respiratory sound or abnormal respiratory sound, to each respiratory sound sample. By using an optimization method such as the steepest descent method or the Newton method, a load and a constant with which the best discrimination between respiratory normality and respiratory abnormality is made can be generated. The generated load $s_m$ and the constant d are stored in the respiratory abnormality degree load storage unit 185.

[Determination of Respiratory Abnormality]

Referring back to FIG. 2, the respiratory abnormality determination section 190 will be described. The respiratory abnormality determination section 190 determines whether respiratory sound is in the normal respiratory condition or the abnormal respiratory condition on the basis of the respiratory abnormality degree Z(l) generated by the respiratory abnormality degree generation section 180. For example, as described below, it can be determined that respiratory sound is in the abnormal respiratory condition when the respiratory abnormality degree Z(l) is equal to or larger than a predetermined threshold value TH2 and respiratory sound is in the normal respiratory condition when the respiratory abnormality degree Z(l) is not equal to or larger than the threshold value TH2.

$Z(l) \geq TH2 \rightarrow$ abnormal respiratory condition $Z(l) < TH2 \rightarrow$ normal respiratory condition In addition, using two threshold values TH3 and TH4, a warning condition may be set as an intermediate condition as described below.

$Z(l) \geq TH3 \rightarrow$ abnormal respiratory condition $TH4 \leq Z(l) < TH3 \rightarrow$ warning condition $Z(l) < TH4 \rightarrow$ normal respiratory condition

[Respiratory Condition Analysis Method]

Figure 10:
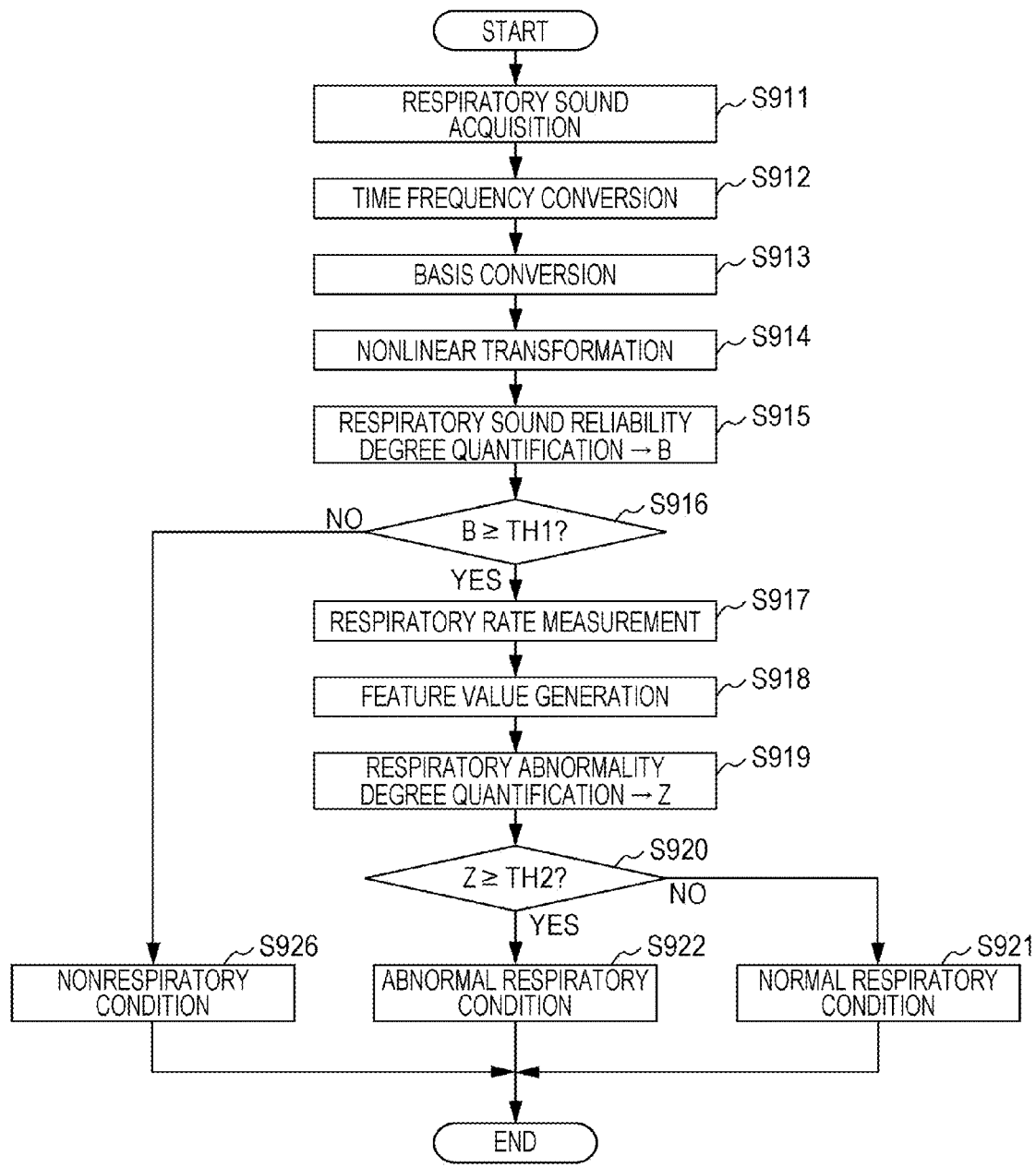
FIG. 10 is an exemplary flowchart of a respiratory condition analysis method according to an embodiment of the present disclosure.

FIG. 10 is an exemplary flowchart of a respiratory condition analysis method according to an embodiment of the present disclosure. The respiratory signal acquisition section 110 acquires a time-series respiratory signal including respiratory sound of a living body such as a human being (step S911). The time frequency conversion unit 121 performs time frequency conversion on the acquired respiratory signal and generates the time frequency signal X(t, k) that is a signal at a time t and a frequency k (step S912). The basis conversion unit 122 projects the generated time frequency signal X(t, k) into the n-dimensional basis vector $w_n(k)$ of a respiratory sound model (step S913). The nonlinear transformation unit 123 performs nonlinear transformation on the basis conversion signal Y(t, n) obtained by the projection and outputs the respiratory sound correlation degree Q(t, n) (step S914).

The respiratory sound reliability degree generation section 130 performs a linear weighted sum on the output respiratory sound correlation degree Q(t, n) and quantifies the respiratory sound reliability degree B(t) (step S915). A respiratory segment is identified on the basis of the respiratory sound reliability degree B(t) (step S916). That is, when the respiratory sound reliability degree B(t) is smaller than the threshold value TH1 (No in step S916), it is determined that a nonrespiratory condition is set (step S926).

On the other hand, when the respiratory sound reliability degree B(t) is equal to or larger than the threshold value TH1 (Yes in step S916), it is determined that a respiratory condition is set and the respiratory rate measurement section 150 measures the number of respirations (step S917). The feature value generation section 160 generates m kinds of feature values S(l, m) of the respiratory signal for each respiratory segment l (step S918). The respiratory abnormality degree generation section 180 quantifies the respiratory abnormality degree Z(l) by performing the linear weighted sum of the feature values S(l, m) (step S919).

On the basis of the quantified respiratory abnormality degree z(l), the respiratory abnormality determination section 190 determines whether respiratory sound is in a normal respiratory condition or an abnormal respiratory condition (step S920). That is, when the respiratory abnormality degree Z(l) is equal to or larger than the threshold value TH2 (Yes in step S920), it is determined that respiratory sound is in the abnormal respiratory condition (step S922). On the other hand, when the respiratory abnormality degree Z(l) is smaller than the threshold value TH2 (No in step S920), it is determined that respiratory sound is in the normal respiratory condition (step S921). Here, an exemplary case in which the conditions of respiratory sound are classified into the normal respiratory condition and the abnormal respiratory condition has been described. As described previously, a warning condition may be set as an intermediate condition.

Thus, according to the first embodiment of the present disclosure, by quantifying the respiratory abnormality degree Z(l) on the basis of the feature values S(l, m) in an identified respiratory segment, respiratory abnormality can be determined on the basis of the quantified respiratory abnormality degree.

2. Second Embodiment

Schematic Configuration of Respiratory Condition Analysis Apparatus

Figure 11:
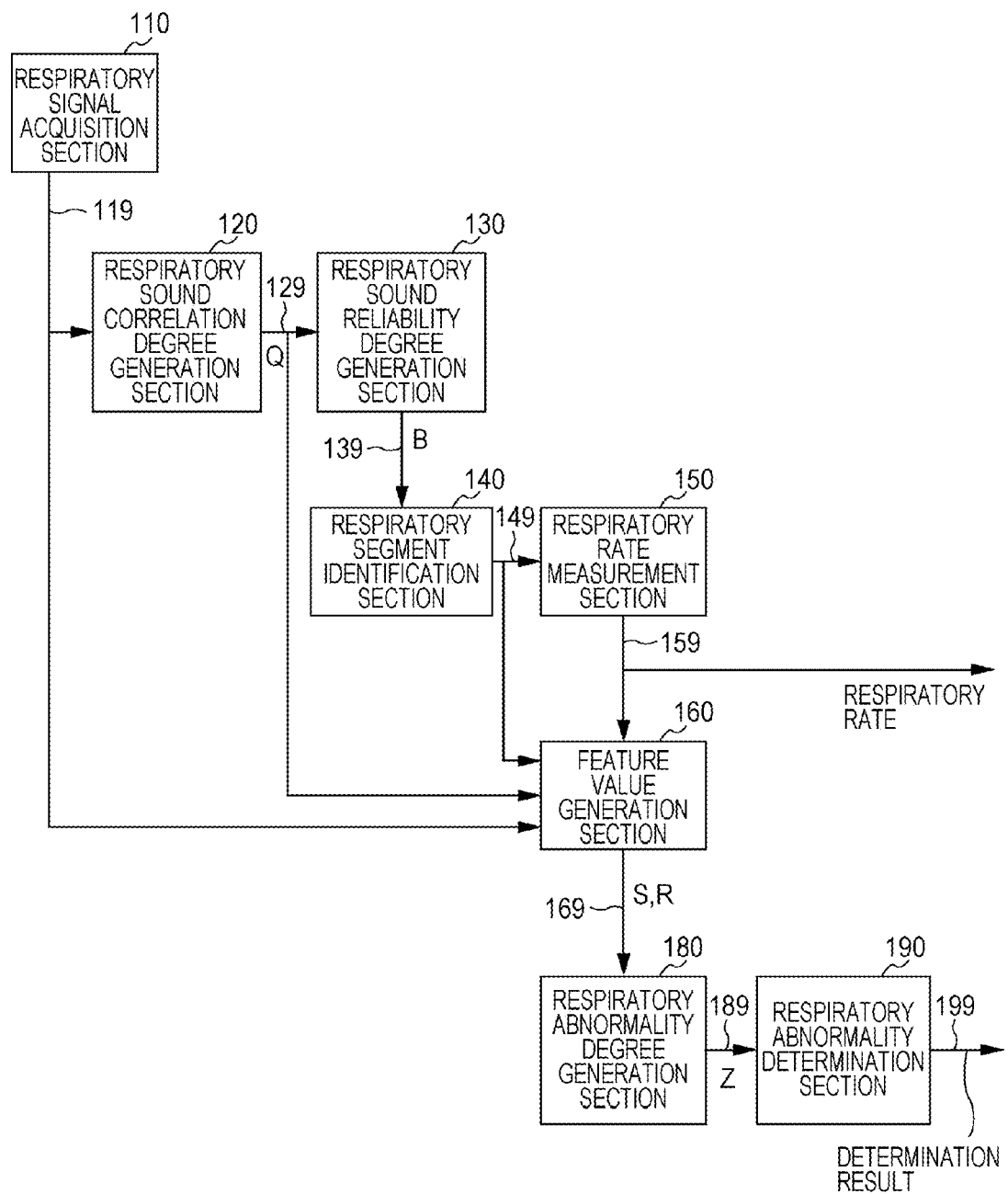
FIG. 11 is a diagram illustrating an exemplary configuration of a respiratory condition analysis apparatus according to a second embodiment of the present disclosure.

FIG. 11 is a diagram illustrating an exemplary configuration of the respiratory condition analysis apparatus 30 according to the second embodiment of the present disclosure. The respiratory condition analysis apparatus 30 according to the second embodiment differs from a respiratory condition analysis apparatus according to the first embodiment in that the respiratory sound correlation degree Q(t, n) generated by the respiratory sound correlation degree generation section 120 is input into the feature value generation section 160. That is, the feature value generation section 160 according to the second embodiment generates not only the feature value S(l, m) of a respiratory segment but also a feature value R(l, n) based on the respiratory sound correlation degree Q(t, n) of a corresponding respiratory segment 1. In the second embodiment, the respiratory sound correlation degree Q(t, n) that is intended to be used for identification of a respiratory segment is used for determination of respiratory abnormality.

A single respiratory segment has a plurality of respiratory sound correlation degrees Q(t, n). By performing averaging, weighted averaging with a window function, or mean square on the respiratory sound correlation degrees Q(t, n) of a target respiratory segment, the feature value R(l, n) can be generated. These averaging methods may be used in combination.

The respiratory abnormality degree generation section 180 according to the second embodiment quantifies the respiratory abnormality degree Z(l) on the basis of the feature values S(l, m) and R(l, n). In order to quantify the degree of respiratory abnormality, a so-called statistical identification method can be used as described previously. For example, in the case of a linear discrimination apparatus, the respiratory abnormality degree Z(l) can be quantified by the linear weighted sum of feature values as represented by the following equation.

$$Z(l) = \sum_n r_n R(l, n) + \sum_m s_m S(l, m) + d$$

A load $r_n$ is generated in a learning process similar to that in which the load $s_m$ is generated, and is stored in the respiratory abnormality degree load storage unit 185 in advance.

A respiratory condition analysis method according to the second embodiment is the same as that according to the first embodiment described with reference to FIG. 10 except that the feature value R(l, n) is generated in step S918 and is used for the quantification of the degree of respiratory abnormality in step S919.

Thus, according to the second embodiment, the degree of respiratory abnormality is quantified using not only the feature value S(l, m) of a respiratory segment but also the feature value R(l, n) based on a respiratory sound correlation degree, and respiratory abnormality can be determined on the basis of the quantified degree of respiratory abnormality.

The embodiments of the present disclosure have been described as an example for embodying the present disclosure, and as described in the embodiments of the present disclosure, the matters according to the embodiments of the present disclosure individually correspond to disclosure-defining matters in the claims. Similarly, the disclosure-defining matters in the claims correspond to the matters according to the embodiments of the present disclosure having the same names as the disclosure-defining matters. However, the present disclosure is not limited to the embodiments, and various modifications can be made to the embodiments without departing from the scope of the present disclosure.

In addition, the processing procedures described in the embodiments of the present disclosure may be considered to be a method including a series of the processing procedures, a program for causing a computer to execute the series of the processing procedures, or a recording medium storing the program. As the recording medium, for example, a CD (Compact Disc), an MD (MiniDisc), a DVD (Digital Versatile Disk), a memory card, a Blu-ray Disc (registered trademark), or the like may be used.

The present disclosure contains subject matter related to that disclosed in Japanese Priority Patent Application JP 2010-273635 filed in the Japan Patent Office on Dec. 8, 2010, the entire contents of which are hereby incorporated by reference.

What is claimed is:

1. A respiratory condition analysis apparatus comprising:
one or more processors configured to:
acquire a time-series respiratory signal including respiratory sound of a living body, wherein the time-series respiratory signal is measured by one or more sensors coupled to the living body;
generate a degree of correlation between a respiratory sound model set in advance and the respiratory signal;
generate a degree of reliability of the respiratory sound representing respiratory sound likeness of the respiratory signal on the basis of the correlation degree;
identify a respiratory segment that is a time segment including the respiratory sound in the respiratory signal, wherein the respiratory segment is identified on the basis of the respiratory sound reliability degree;
generate a predetermined feature value of the respiratory signal for the identified respiratory segment; and
generate a degree of abnormality of the respiratory sound included in the respiratory signal on the basis of the feature value,
wherein a time frequency signal is generated by performing a time frequency conversion on the respiratory signal, the time frequency signal is projected into a basis vector of the respiratory sound model and a basis conversion signal is generated, and a predetermined nonlinear transformation is performed on the basis conversion signal to output the correlation degree.

2. The respiratory condition analysis apparatus according to claim 1, wherein the one or more processors are configured to determine whether the respiratory sound is in a normal respiratory condition or an abnormal respiratory condition on the basis of the generated abnormality degree.

3. The respiratory condition analysis apparatus according to claim 2, wherein the one or more processors are configured to determine an intermediate condition between the normal respiratory condition and the abnormal respiratory condition.

4. The respiratory condition analysis apparatus according to claim 1, wherein the one or more processors are configured to measure a number of the identified respiratory segments per unit time and output a result of the measurement as a number of respirations.

5. A respiratory condition display apparatus comprising:
one or more processors configured to:
acquire a time-series respiratory signal including respiratory sound of a living body, wherein the time-series respiratory signal is measured by one or more sensors coupled to the living body;
generate a basis conversion signal based on a projection of a time frequency signal of the respiratory signal into a basis vector of a respiratory sound model;
identify a respiratory segment that is a time segment including the respiratory sound in the respiratory signal, wherein the respiratory segment is identified on the basis of the generated basis conversion signal;
generate a predetermined feature value of the respiratory signal for the identified respiratory segment;

generate a degree of abnormality of the respiratory sound included in the respiratory signal on the basis of the generated predetermined feature value;

determine whether the respiratory sound is in a normal respiratory condition or an abnormal respiratory condition on the basis of the generated abnormality degree; and display a result of the determination of the respiratory sound on a display screen.

6. A respiratory condition analysis method comprising:

in a computing device:
  acquiring a time-series respiratory signal including respiratory sound of a living body, wherein the time-series respiratory signal is measured by one or more sensors coupled to the living body;
  generating a basis conversion signal based on a projection of a time frequency signal of the respiratory signal into a basis vector of a respiratory sound model;
  identifying a respiratory segment that is a time segment including the respiratory sound in the respiratory signal, wherein the respiratory segment is identified on the basis of the generated basis conversion signal;
  generating a predetermined feature value of the respiratory signal for the identified respiratory segment; and
  generating a degree of abnormality of the respiratory sound included in the respiratory signal on the basis of the generated predetermined feature value.

7. A non-transitory computer readable storage medium, having stored thereon, a set of computer-executable instructions that causes a computer perform the steps comprising:
  acquiring a time-series respiratory signal including respiratory sound of a living body, wherein the time-series respiratory signal is measured by one or more sensors coupled to the living body;
  generating a basis conversion signal based on a projection of a time frequency signal of the respiratory signal into a basis vector of a respiratory sound model;
  identifying a respiratory segment that is a time segment including the respiratory sound in the respiratory signal, wherein the respiratory segment is identified on the basis of the generated basis conversion signal;
  generating a predetermined feature value of the respiratory signal for the identified respiratory segment; and
  generating a degree of abnormality of the respiratory sound included in the respiratory signal on the basis of the generated predetermined feature value.

8. The respiratory condition display apparatus according to claim 5, wherein the generated predetermined feature value of the respiratory signal comprises one of: a signal amplitude value, a change in the signal amplitude value, a spectrum value, a change in the spectrum value, a zero-crossing rate and/or a change in the zero-crossing rate.

9. The respiratory condition display apparatus according to claim 5, wherein the generated basis conversion signal represents a degree of similarity between frequency spectra of the respiratory sound and the respiratory sound model.

10. The respiratory condition display apparatus according to claim 5, wherein the one or more processors are configured to generate a degree of correlation between the respiratory sound model and the respiratory signal by performing a predetermined non-linear transformation of the generated basis conversion signal.

11. The respiratory condition display apparatus according to claim 10, wherein the one or more processors are configured to generate a degree of reliability of the respiratory sound representing respiratory sound likeness of the respiratory signal on the basis of the generated degree of correlation.

12. The respiratory condition display apparatus according to claim 11, wherein the one or more processors are configured to generate the degree of reliability by performing a linear weighted sum of a plurality of degrees of correlation.

13. The respiratory condition display apparatus according to claim 11,
  wherein the respiratory segment is identified by determining a transition between a respiratory condition and a non-respiratory condition,
  wherein the respiratory condition is determined when the generated degree of reliability is equal to or greater than a predetermined threshold value and the non-respiratory condition is determined when the generated degree of reliability is less than the predetermined threshold value.

14. The respiratory condition display apparatus according to claim 5, wherein the basis vector of the respiratory sound model is determined based on a teacher signal and a sound sample.

* * * * *